United States Patent
Sugita et al.

(10) Patent No.: US 6,685,685 B2
(45) Date of Patent: Feb. 3, 2004

(54) DISPOSABLE EXCRETA MANAGEMENT DEVICE

(75) Inventors: Masataka Sugita, Osaka (JP); Maki Hyodo, Kobe (JP)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/439,547

(22) Filed: May 16, 2003

(65) Prior Publication Data

US 2003/0204177 A1 Oct. 30, 2003

Related U.S. Application Data

(63) Continuation of application No. PCT/US00/34389, filed on Dec. 18, 2000.

(51) Int. Cl.⁷ .................................................. A61F 5/44
(52) U.S. Cl. .............................. 604/355; 604/385.19
(58) Field of Search ........................ 604/385.19, 355, 604/348

(56) References Cited

U.S. PATENT DOCUMENTS

| | | | |
|---|---|---|---|
| 4,445,898 A | 5/1984 | Jensen | |
| 4,784,656 A | * 11/1988 | Christian | 604/355 |
| 4,950,262 A | 8/1990 | Takagi | |
| 5,527,303 A | 6/1996 | Milby, Jr. et al. | |
| 6,133,501 A | * 10/2000 | Hallock et al. | 604/369 |
| 6,168,584 B1 | * 1/2001 | Allen et al. | 604/385.19 |
| 6,395,955 B1 | * 5/2002 | Roe et al. | 604/361 |
| 2002/0082570 A1 | * 6/2002 | Mishima et al. | 604/332 |
| 2002/0128614 A1 | * 9/2002 | Cinelli et al. | 604/332 |
| 2002/0138058 A1 | * 9/2002 | Mishima et al. | 604/385.19 |

FOREIGN PATENT DOCUMENTS

EP    0 245 064 A2    11/1987

* cited by examiner

Primary Examiner—Weilun Lo
Assistant Examiner—Michael G Bogart
(74) Attorney, Agent, or Firm—Kevin C. Johnson

(57) ABSTRACT

A disposable excreta management device has a longitudinal centerline and a transverse centerline, and comprises a flexible bag to contain excreta and an adhesive flange to attach the device to the body of the wearer. The flexible bag has a wearer facing portion and a garment facing portion. The wearer facing portion has an opening surrounded by the adhesive flange. The disposable excreta management device is characterized in that expansibility of the garment facing portion of the flexible bag is greater than that of the wearer facing portion of the flexible bag when the flexible bag contains excreta.

9 Claims, 15 Drawing Sheets

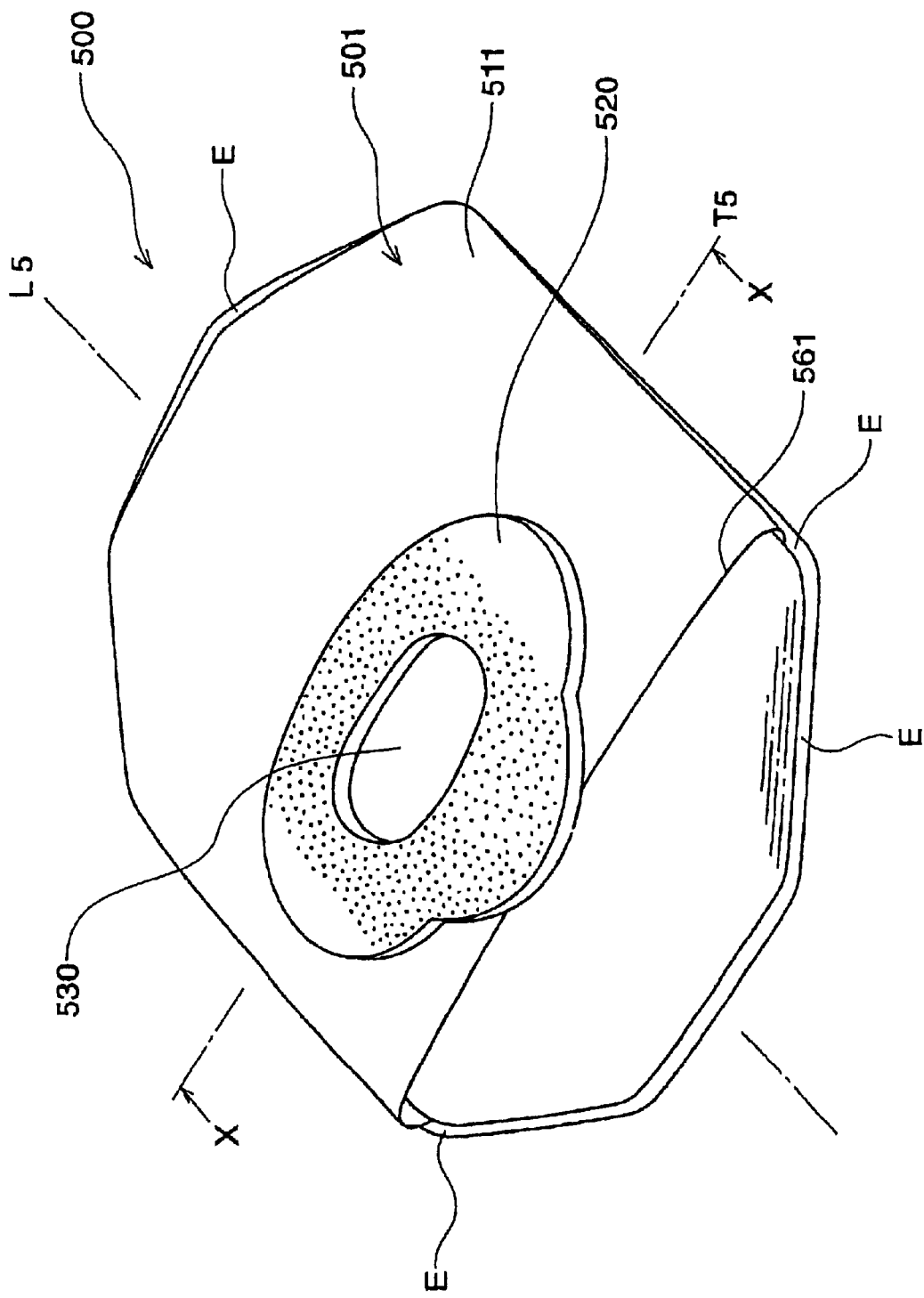

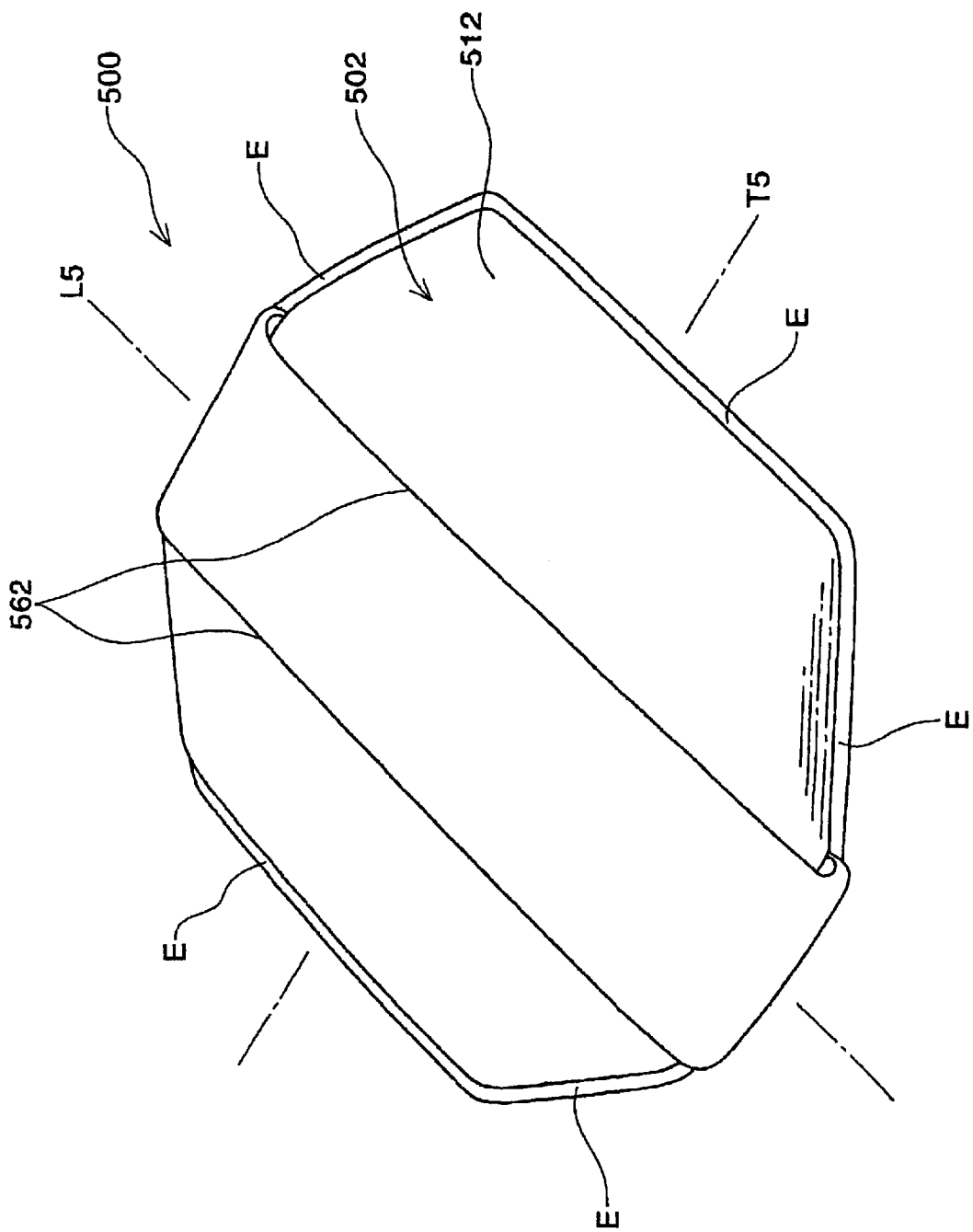

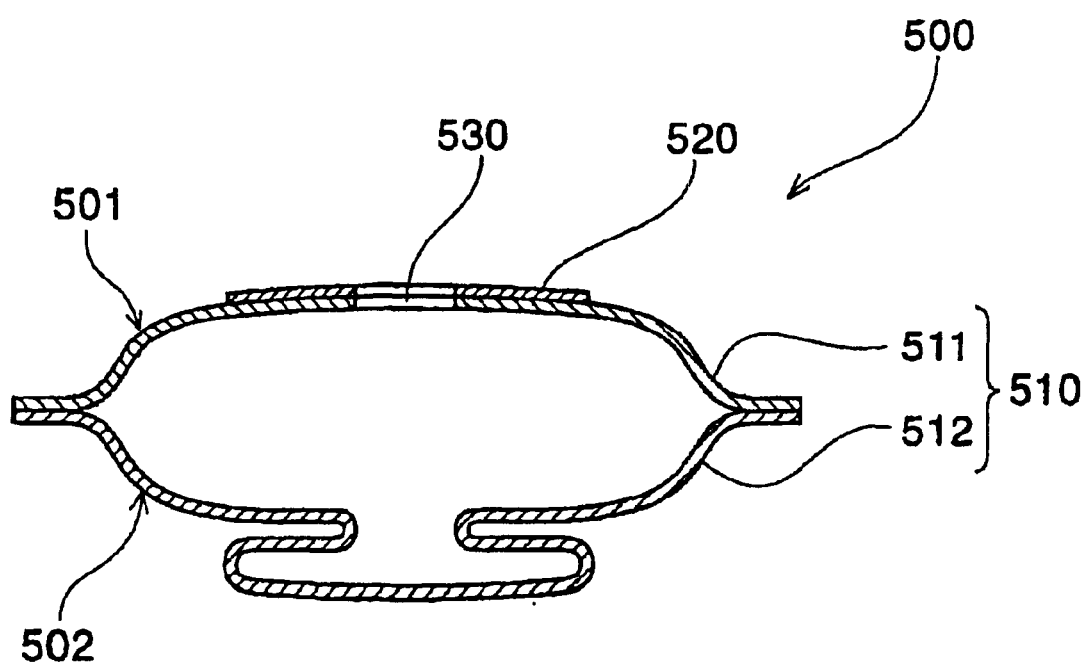

DISPOSABLE EXCRETA MANAGEMENT DEVICE

CROSS REFERENCE TO RELATED REFERENCES

This is a continuation of International Application PCT/US00/34389 with an International filing date of Dec. 18, 2000.

FIELD OF THE INVENTION

The present invention relates to a disposable excreta management device such as an urine management device and a fecal management device, for babies, children or adults. In particular, the present invention relates to a disposable excreta management device comprising a skin attachment means and a flexible pouch which can expand vertically to have a three-dimensional shape in use.

BACKGROUND

Excreta management devices are known articles of manufacture that are designed to be worn principally by infants, incontinence sufferers or bedridden patients. Such excreta management devices are attached to the urethral region, the natural anal region or artificial anus of the wearer and are intended to entrap and immediately contain urine, fecal material or other bodily discharges.

A representative fecal management device is disclosed in, e.g., EP 0245064. It discloses a fecal incontinence bag having flexible front and rear walls secured together around their periphery. The front wall has a hole therein for entry of matter discharged by the wearer. The hole is surrounded by an adhesive pad of skin-compatible water-resistant material secured to the external surface of the front wall surrounding the hole. The general shape of the front and rear wall is rectangular, i.e. the bag has two opposed long sides and two opposed short sides, the width of the bag being relatively short compared to the length of the bag.

Another representative fecal management device is disclosed in, e.g., WO 99/00085 and WO 99/00086. These publications disclose a fecal management device comprising a bag having an aperture and an anatomically-shaped flange which surrounds the aperture. The bag has a wearer facing portion and a garment facing portion, both of which comprise separate pieces of material. The wearer facing portion and the garment facing portion are sealed at the periphery of the bag. In additoin, WO 99/00085 discloses that the surface area of the wearer facing portion is greater than that of the garment facing portion.

A representative urine collector device is disclosed in, e.g., U.S. Pat. No. 4,804,377. It discloses a urine collector device for infants or small children having a flexible collection bag and an adhesively-faced attachment member joined to the bag. The flexible collection bag comprises an inner bag and an outer bag. The inner and outer bags are joined at a common top seam and opposite shared side searns. However, there is no technical idea regarding the expansibility of the collection bag.

Another representative urine management device containing an absorbent material is disclosed in, e.g., WO 00/00113. It discloses a urine management device for infants, adults, for bedridden patients or active patients, having a flexible collection bag, an adhesive flange joined to the bag and an absorbent material to be contained within the bag. The flexible collection bag of the urine management device has a wearer facing portion and a garment facing portion. Furthermore, plural folds are provided on the wearer facing portion of the bag such that the wearer facing portion of the collection bag can expand vertically.

The excreta management devices are generally located in the space between legs of a wearer during use of the device. Therefore, the bag of the device preferably needs to be flexible so as to adapt the bag to the wearer's movement. The bag of the device may be pressed by buttocks and/or legs of the wearer after the wearer discharges excreta, such as urine, fecal material and/or other bodily discharges into the bag. This may cause the excreta in the bag to leak from the inside of the bag to the outside. It is an essential functionality for the excreta management device to expand the bag efficiently so as to avoid leaking of excreta as the bag containing excreta is pressed by wearer's body, such as buttocks and/or legs. While the bag disclosed in WO 00/00113 has plural folds on the wearer facing portion of the bag to expand vertically when excreta are contained into the bag, the garment facing portion of the bag is not provided with any structure to expand. In this structure, the garment facing portion may expand completely ahead of the wearer facing portion when the bag pressed by wearer's body. Therefore, the garment facing portion may prevent the wearer facing portion from expanding completely if the bag is pressed by wearer's body. This is because expansibility of the garment facing portion is not greater than that of the wearer facing portion. In the manner as stated above, none of the publications above disclose how to ensure expansion of the flexible bag in order to avoid leaking of excreta even if the bag is pressed by wearer's body. Thus, none of the existing arts provided all of the advantages and benefits of the present invention.

SUMMARY

The present invention relates to a disposable excreta management device having a longitudinal centerline and a transverse centerline, and comprising a flexible bag to contain excreta and an adhesive flange to attach the device to the body of the wearer. The flexible bag has a wearer facing portion and a garment facing portion. The wearer facing portion has an opening surrounded by the adhesive flange. The disposable excreta management device is characterized in that expansibility of the garment facing portion of the flexible bag is greater than that of the wearer facing portion of the flexible bag when the flexible bag contains excreta.

BRIEF DESCRIPTION OF THE DRAWINGS

While the Specification concludes with claims which particularly point out and distinctly claim the invention, it is believed the present invention will be better understood from the following description of preferred embodiments taken in conjunction with the accompanying drawings, in which like reference numerals identify identical elements and wherein:

FIG. 5A is a top perspective view of another embodiment of a disposable excreta management device;

FIG. 5B is bottom a perspective view of another embodiment of a disposable excreta management device; and FIG. 5C is a cross-sectional view taken along line X—X of FIG. 5A.

DETAILED DESCRIPTION

All cited references are incorporated herein by reference in their entireties. Citation of any reference is not an admission regarding any determination as to its availability as prior art to the claimed invention.

The definitions of several terms are first provided to assist the reader in understanding the present invention.

The term "comprising" means that other steps and other ingredients which do not affect the end result can be added. This term encompasses the term "consisting of" and "consisting essentially of". The term "disposable" as used herein describes devices which generally are not intended to be laundered or otherwise restored or reused (i.e., they are intended to be discarded after a single use and, preferably, to be recycled, composted or otherwise disposed of in an environmentally compatible manner.) The term "nonwoven", as used herein, refers to fabrics made of fibers held together by interlocking or bonding which are not woven, knitted, felted, or the like. (The term "fabric", as used herein, may refer to a nonwoven web, a woven material, or other types of fabrics.) The term "longitudinal", as used herein, refers to a line, axis or direction in the plane of the disposable excreta management device that is generally aligned with (e.g., approximately parallel to) a vertical plane which bisects a standing wearer into left and right body halves when the disposable excreta management device is worn. The terms "transverse" or "lateral" used herein, are interchangeable, and refer to a line, axis or direction which lies within the plane of the disposable excreta management device that is generally perpendicular to the longitudinal direction. As used herein, the term "polyhedron" refers to a three-dimensional shape formed by four or more plane faces, such as tetrahedron, pentahedron, hexahedron, octahedron, cube, prism, pyramid, and composite shapes thereof.

Figure 1A:
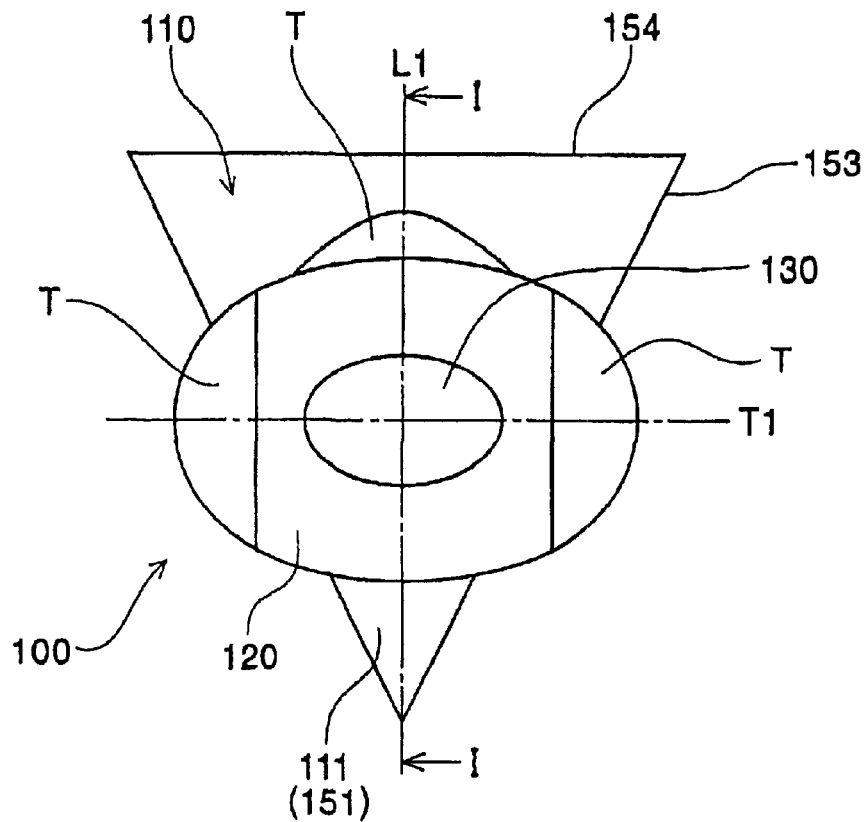
FIG. 1A is a top plan view of one embodiment of a disposable excreta management device.

Referring now to FIGS. 1A–1E, there is shown a preferable embodiment of a disposable excreta management device of the present invention. As shown in FIG. 1A, the disposable excreta management device (100) has two centerlines, one is a longitudinal centerline (L1) and the other is a transverse centerline (T1). The disposable excreta management device (100) comprises a bag (110) having an opening (130) and a flange (120) surrounding the opening (130).

The bag (110) as used herein is a flexible receptacle for the containment of discharged excreta such as urine and/or bowel movement. The bag (110) can be provided in any shape or size depending on the intended use thereof, i.e. whether the device is intended for bedridden patients or active patients suffering from incontinence. For example elongated bags which are principally tubular or rectangular are typically utilized by bedridden patients and elderly incontinence sufferers. For more active wearers whether infants or adults, the excreta management device should preferably be anatomically shaped such that the device follows the contours of the body and can be worn inconspicuously by the wearer under normal garments. Particularly, preferred shapes are three-dimensional shaped bags, such as triangle shaped bags, cone shaped bags, truncated cone shaped bags and pyramidal or truncated pyramidal shaped bags. Further, the bag (110) may have a substantial circular or T shape when the bag (110) is not expand. In a preferred embodiment shown in FIGS. 1A to 1C, the bag (110) is a substantial tetrahedron including a plurality of shape corners.

The bag (110) is preferably designed to provide sufficient volume for excreta under a variety of wearing conditions, also when worn by a freely moving, i.e., not bedridden wearer. The bag (110) is designed to safely contain any entrapped material, typically it will be liquid impermeable, yet it may be breathable. The bag is designed of sufficient strength to resist rupturing in use.

Depending on the shape of the bag (110) required, the bag may be made from a unitary piece of material or from a number of separate pieces of material, which may be identical or different and which are sealed at their respective peripheries.

The bag (110) can comprise one or multiple layers, preferably two or three layers. The layer on the inside of the bag, which will typically at least partially come in contact with excreta, is called the inner layer. The outermost layer of the bag (110), which will typically at least partially come in contact with the skin of the wearer and the garments of the wearer, is called the outer layer. The layer of the bag material may be provided from any material so that the bag is liquid impervious. The layer may in particular comprise any material such as a nonwoven or a polymeric film. In a preferred embodiment, the layer may be formed from a laminate comprising a nonwoven layer and a polymeric film. The outer layer of the bag (110) is preferably provided with a nonwoven layer. The nonwoven outer layer presents an uneven surface to the skin of the wearer and thus significantly reduces the problem of occlusion and greatly improves skin healthiness. In one preferred embodiment, the bag (110) comprises two layers. Preferably the outer layer comprises a nonwoven layer and the inner layer comprises a film. Alternatively, the bag (110) comprises three layers; one film layer and two nonwoven layers. The film may be interposed between the two nonwoven layers. This sequence of layers results in a closed fibrous structure, which has a particularly pleasing sensation on contact with the skin of the wearer.

Suitable nonwoven layers may comprise felt fabrics, spunlaced fabrics, fluid jet entangled fabrics, air-laid fabrics, wet-laid fabrics, dry-laid fabrics, melt-blown fabrics, staple fiber carding fabrics, spunbonded fabrics, stitch-bonded fabrics, apertured fabrics, combinations of the above or the like. The nonwoven layer or the nonwoven layers constituting the bag (110) may be hydrophobic or hydrophilic. For example, if the bag comprises a film layer, the nonwoven layers may be hydrophilic or hydrophobic. If the bag does not comprise a film layer, preferably at least one nonwoven layer is hydrophobic. It may even be desirable to make both nonwoven layers hydrophobic to ensure that the bag is liquid impervious. Typically, the nonwoven layer is treated with a surface active material, such as a fluorochemical or other hydrophobic finishings, to provide the requisite hydrophobicity. The nonwoven layer, however, may equally be treated with coatings of liquid impervious materials such as hot-melt adhesives or coatings of silicone or other hydrophobic compounds such as rubbers and vegetable and mineral waxes or it may be physically treated using nanoparticulates or plasma coating techniques, for example. The nonwoven layer can also be treated with agents to improve the tactile perceivable softness. The agents include but are not limited to vegetable, animal or synthetic oils, silicone oils and the like. The presence of these agents are known to impart a silky or flannel-like feel to the nonwoven layer without rendering it greasy or oily to the tactile sense of the wearer. Additionally, surfactant material, including anionic, non-anionic, cationic and non-cationic surfactants, may be added to further enhance softness and surface smoothness. Furthermore, the nonwoven layer may be impregnated with a lotion to provide desirable therapeutic or protective coating lotion benefits. The lotion coating is transferable to the skin of the wearer by normal contact and wearer motion and/or body heat. Generally, mineral oil in the form of a lotion is recognized as being effective in imparting a soothing, protective coating to the skin of the wearer. It is also possible to impregnate the nonwoven layer with a solid oil phase of cream formulation or to incorporate into the nonwoven layer an array of pressure- or thermal- or hydrorupturable capsules containing for example, baby oil.

Suitable film materials may comprise a thermoplastic material. The thermoplastic material can be selected from among all types of polyolefins especially polyethylene, polypropylene, amorphous polyolefins, and the like; material containing meltable components comprising fibers or polymeric binders including natural fibers such as cellulose—wood pulp, cotton, jute, hemp; synthetic fibers such as fiberglass, rayon, polyester, polyolefin, acrylic, polyamid, aramid, polytetrafluroethylene metal, polyimide; binders such as bicomponent high melt/low melt polymer, copolymer polyester, polyvinyl chloride, polyvinyl acetate/ chloride copolymer, copolymer polyamide, materials comprising blends wherein some of the constituent materials are not meltable; air and vapour permeable materials including microporous films such as those supplied by EXXON Chemical Co., Ill, US under the designation EXXAIRE or those supplied by Mitsui Chemical Co., Japan under the designation ESPOIR NO; and monolithic breathable materials such as Hytrel™ available from DuPont and Pebax™ available from ELF Atochem, France. In a preferred embodiment, a film which is comprised in any layer is preferably permeable to gases such as air and to vapour such as water vapour in order to avoid the problem of entrapment and condensation of moisture vapour given off by the body of the wearer and thus, the hot, clammy and uncomfortable conditions after a short period of use.

In the embodiment shown in FIGS. 1A–1E, the bag (110) preferably has a three-dimensional shape including a corner (140). Preferably, the bag (110) has a substantial tetrahedron shape, and four surfaces which are (151), (152), (153) and (154). Furthermore, the bag (110) has two portions, one is a wearer facing portion (111) and the other is a garment facing portion (112). The wearer facing portion (111) is the portion of the bag (110), which comprises the opening (130) and is generally oriented towards the wearer when the excreta management device (100) is worn. The wearer facing portion (111) preferably comprises only the plane-like surface (151). The garment facing portion (112) is the portion of the bag (110), which is the generally oriented away from the wearer when the excreta management device (100) is worn, and towards a garment if a garment is worn. The garment facing portion (112) comprises the surfaces (152), (153) and (154), and does not have the opening (130). Further, the garment facing portion (112) is provided with the corner (140) positioned opposite to the wearer facing portion (111).

The bag (110) preferably has at least one fold on the garment facing portion (112). The number of the fold will obviously depend upon the circumstances, such as a configuration of the bag, a size of the bag and a material of the bag. In the embodiment shown in FIG. 1D, the garment facing portion (112) is folded along the fold (160). The bag (110) can expand vertically to have a three-dimensional shape when the bag (110) contains excreta, thereby ensuring better wearing comfort for a moving wearer and providing extra storage capacity in use if needed. Preferably, the fold (160) may be positioned across the opening (130) as shown in FIG. 1E when the bag (110) is folded. This enables excreta discharged toward the opening (130) to directly reach and push the fold (160) to expand the bag (110) vertically and to enter the interior of the bag (110) speedily. Alternatively, it is possible to expand the bag (110) into a three-dimensional shape easily by pulling the corner (140) after the device (100) is attached to the wearer.

The expansibility of the garment facing portion (112) is grater than that of the wearer facing portion (111). This is because the garment facing portion (112) has the fold (160) so that the bag (110) forms the three dimensional shape when the bag (110) expands, and the wearer facing portion (111) comprises only one plane-like surface (151). This structure enables the bag (110) to expand sufficiently even if the bag (110) containing excreta is pressed by wearer's body, such as buttocks and/or legs. Accordingly, it is possible to prevent leakage of excreta in the bag (110) efficiently. The garment facing portion (112) may comprise elastic material, such as elastomer, rubber and polyurethane to have expansibility. The garment facing portion (112) may comprise elastic material without the fold (160), or the garment facing portion (112) comprising elastic material may have the fold (160) as well, as long as the bag (110) expands smoothly when the bag (110) contains excreta.

Figure 1B:
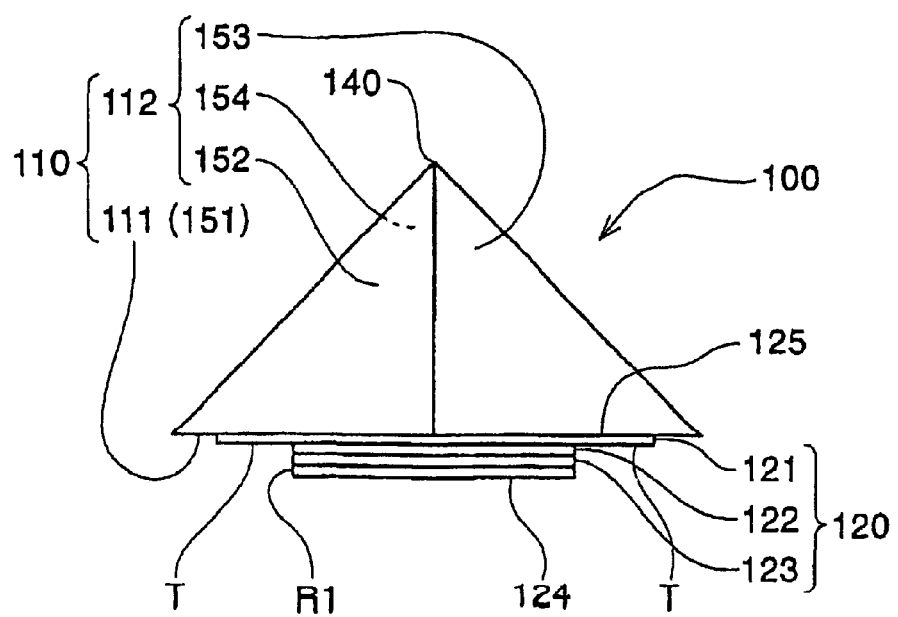
FIG. 1B is a side view of the disposable excreta management device of FIG. 1A.
Figure 1C:
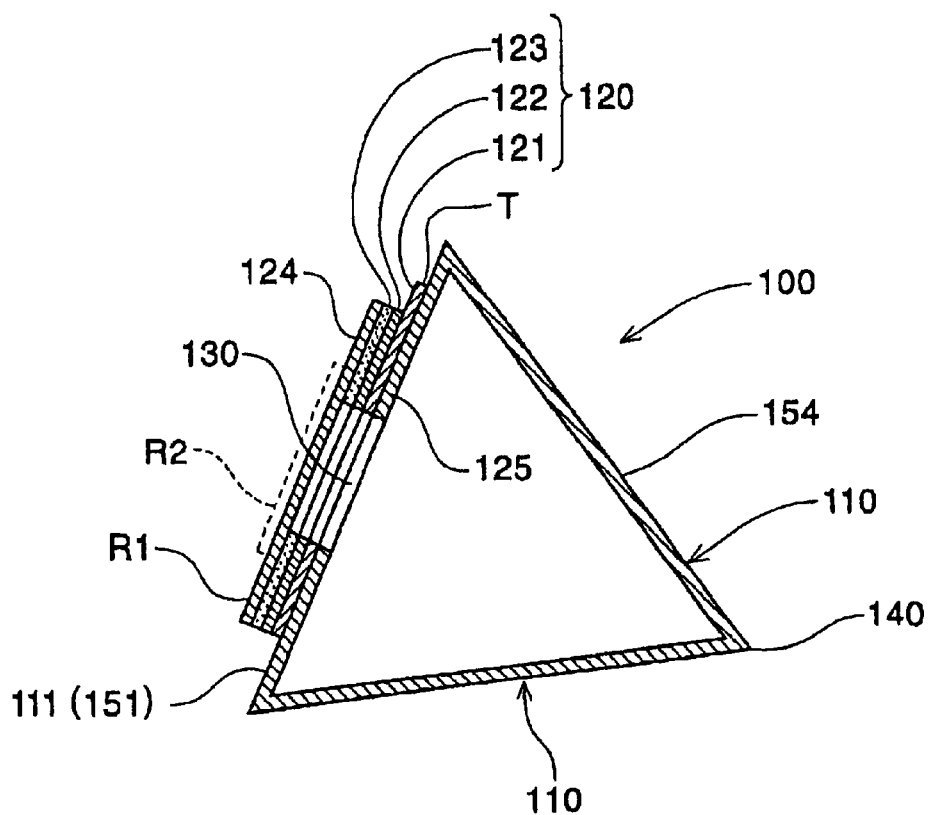
FIG. 1C is a cross-sectional view taken along line I—I of FIG. 1A.
Figure 1D:
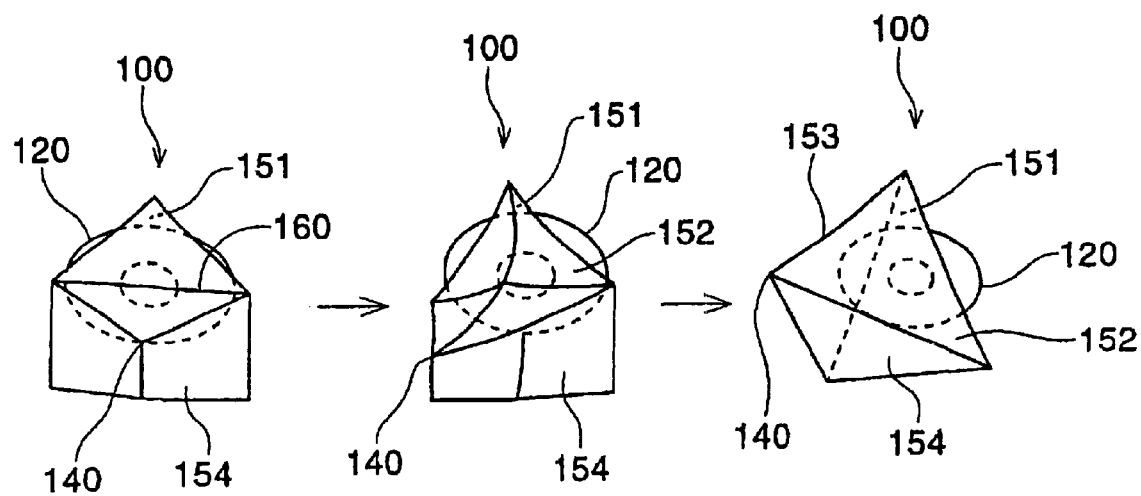
FIG. 1D is a schematic view showing processes for expanding the disposable excreta management device shown in FIGS. 1A–1C.
Figure 1E:
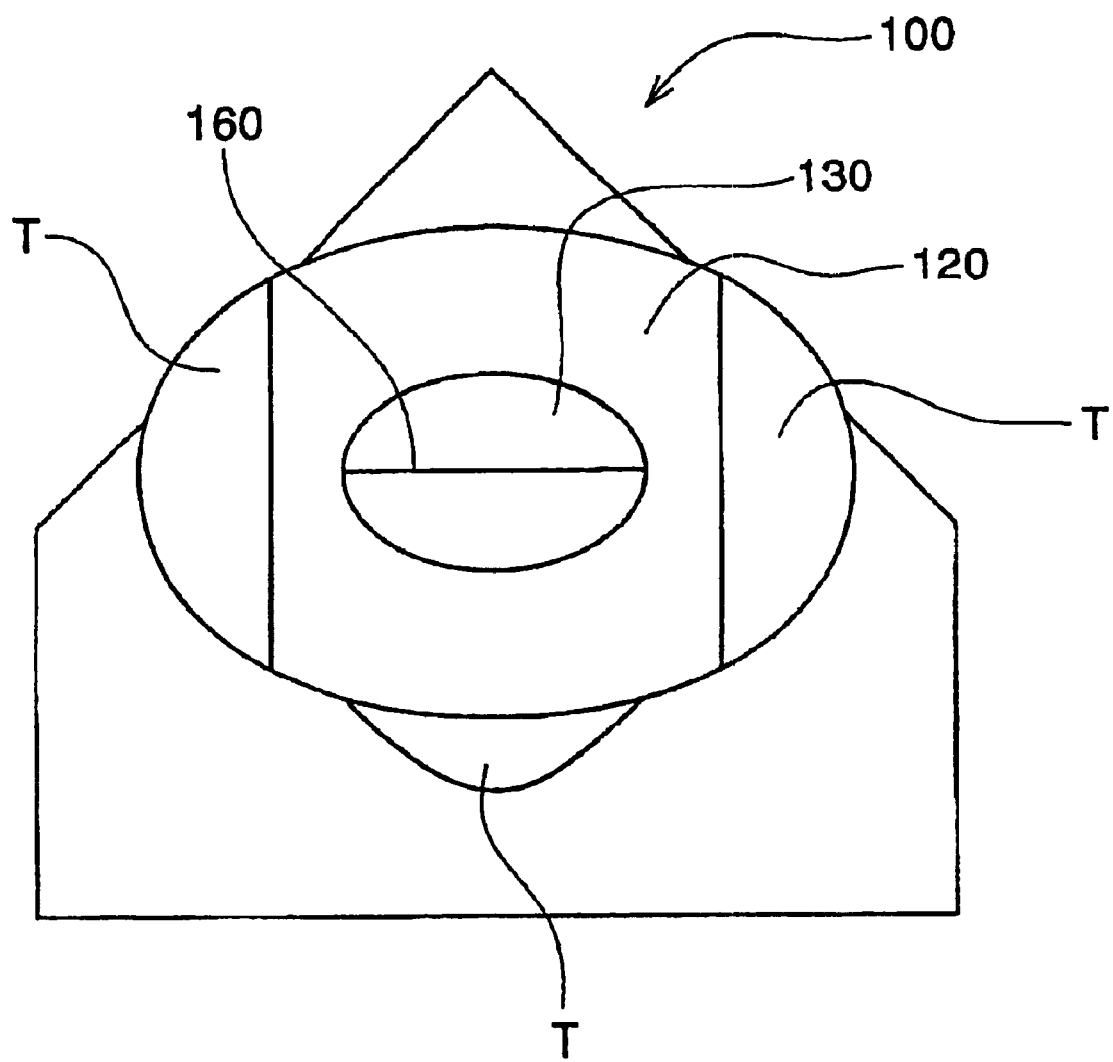
FIG. 1E is a top plan view of the disposable excreta management device shown in FIGS. 1A–1C in a folded configuration.

As shown in FIGS. 1A–1E, the flange (120) (or adhesive flange) is provided at the periphery of the opening (130) to attach the device (100) to the wearer's body. The adhesive flange (120) has a wearer facing side (124) and an opposed garment facing side (125) as shown in FIGS. 1B and 1C. In a preferred embodiment, these are two major, substantially flat surfaces of the adhesive flange (120). The adhesive flange (120) may be provided in any size depending on the wearer group for which the device is intended. The adhesive flange (120) may be provided in any shape and preferably has a symmetrical, slightly oblong shape.

In the embodiment as shown in FIGS. 1B and 1C, the adhesive flange (120) may comprise a nonwoven layer (121), a polyurethane layer (122) and an adhesive layer (123) as shown in FIG. 1C. In this embodiment, both the nonwoven layer (121) and the polyurethane layer (122) may be provided as a substrate in order to support the adhesive layer (123), or a substrate may comprise either of them. Particularly, the polyurethane layer (122) may be provided in order to adapt the devise (100) to the movement of the wearer during use of the device (100).

The adhesive flange (120) should be made of soft, flexible and malleable material to allow easy placement of the flange to the uro-genital area. In addition, the adhesive flange (120) may be made of a hydrophobic material such that if urine does come into contact with the perimeter surrounding opening (130) it is repelled and does not wick to the outer edge of the adhesive flange (120). It is also desirable to construct the adhesive flange (120) from a breathable material to avoid the problem of entrapment and condensation of moisture vapor given off by the body of the wearer and thus, the hot, clammy and uncomfortable conditions after a short period of use. Suitable materials for the adhesive flange (120) include but are not limited to nonwoven materials, and foams, such as open celled thermoplastic foams. An open-cell foam having a thickness within the general range of about 0.5 to 10 millimeters (preferably about 2 millimeters) has been found particularly effective. Other foam materials or other suitable plastics sheet materials having the described properties of such foams (i.e., softness, pliability, stretchability, contractability, breathability, and hydrophobicity) might be used.

The wearer facing side (124) of the adhesive flange (120) comprises a body-compatible adhesive such as the adhesive layer (123) as shown in FIGS. 1B and 1C. The adhesive layer (123) is used in order to fix the device (100) with the wearer's body. In the embodiment as shown in FIGS. 1B and 1C, the adhesive layer (123) is preferably covered with a release film (R1) to protect the adhesive layer (123) from contamination before use, such as siliconized paper or film. If the opening (130) is formed thorough the release film (R1) for the manufacturing reason, a second release film (R2) designated by the broken line in FIG. 1C may be added so that foreign objects do not enter into the bag (110) before use of the device (100). The adhesive layer (123) may cover the entire wearer facing surface of the flange, or alternatively have at least one non-adhesive portion which may be adhesive free or may contain inactivated or covered adhesives.

Preferably, a tab (T) is applied on the adhesive flange (120) in order to remove the device (100) from the wearer's body easily. The tab (T) helps users remove the device (100) from the wearer's body. In addition, the tab (T) may comprise the nonwoven layer (121) and/or the polyurethane layer (122) as shown in FIGS. 1B and 1C.

Any medically approved water resistant pressure sensitive adhesive may be used for the adhesive layer (123) to attach the device to the uro-genital area of the wearer, such as hydrocolloid adhesives and hydrogel adhesives. Particularly effective adhesives in providing the desired adhesive properties to secure the flange to the skin of the wearer at the sensitive uro-genital area, whilst allowing for relatively painless application and removal are hydrophillic hydrogels formed from crosslinking polymers with a plastisicer to form a three-dimensional matrix.

The adhesive can be applied to the wearer facing side (124) of the adhesive flange (120) by any means known in the art such as slot coating, spiral, or bead application or printing. Typically the adhesive is applied at a basis weight of from 20 $g/m^2$ to 2500 $g/m^2$, preferably from 500 $g/m^2$ to 2000 $g/m^2$, more preferably from 700 $g/m^2$ to 1500 $g/m^2$ depending on the end use envisioned. For example for urine management devices to be used for children the amount of adhesive may be less than for urine management devices designed for active adult incontinence sufferers.

The adhesive flange (120) is attached to the wearer facing portion (111) by means known to the man skilled in the art, such as adhesives.

Figure 2A:
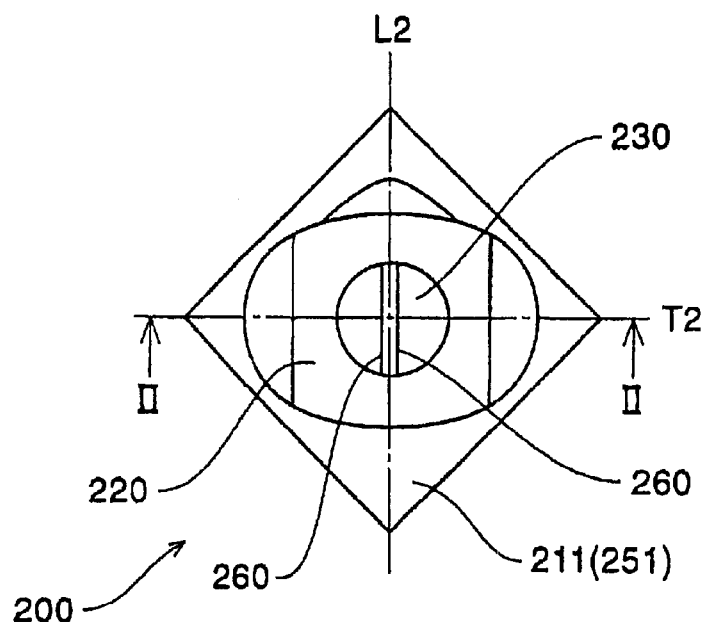
FIG. 2A is a top plan view of another embodiment of a disposable excreta management device.
Figure 2B:
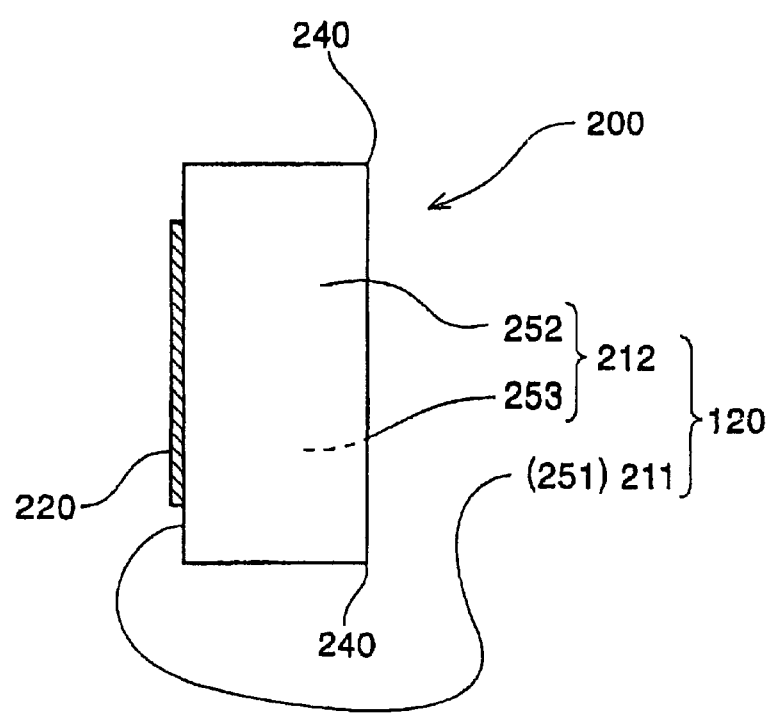
FIG. 2B is a side view of the disposable excreta management device of FIG. 2A.
Figure 2C:
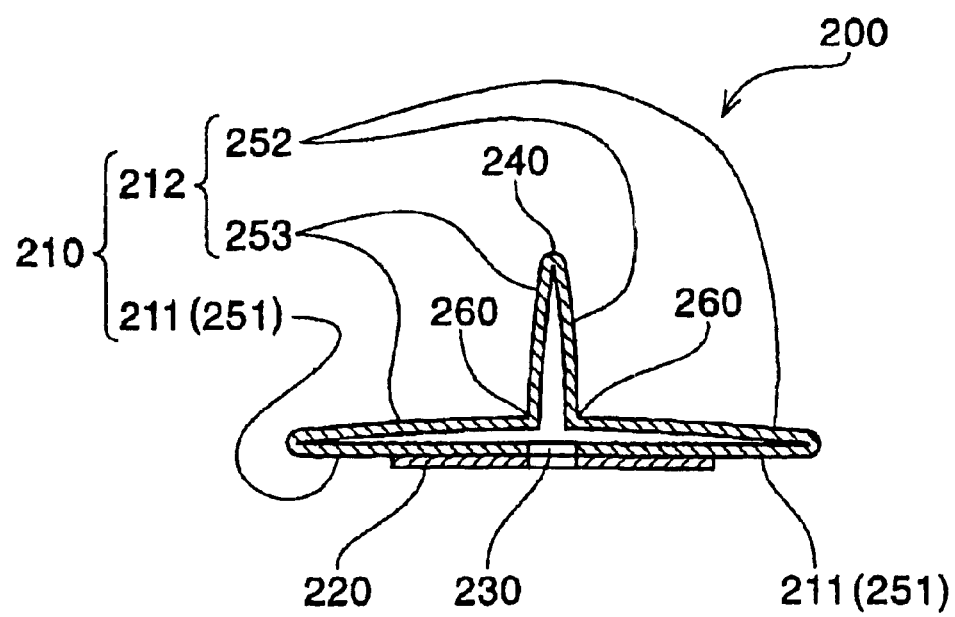
FIG. 2C is a cross-sectional view taken along line II—II of FIG. 2A.

Referring now to FIGS. 2A–2D, there is shown another preferable embodiment of a disposable excreta management device of the present invention. As shown in FIG. 2A, the disposable excreta management device (200) has two centerlines, one is a longitudinal centerline (L2) and the other is a transverse centerline (T2). The disposable excreta management device (200) comprises a bag (210) having an opening (230) and a flange (220) surrounding the opening (230).

Figure 2D:
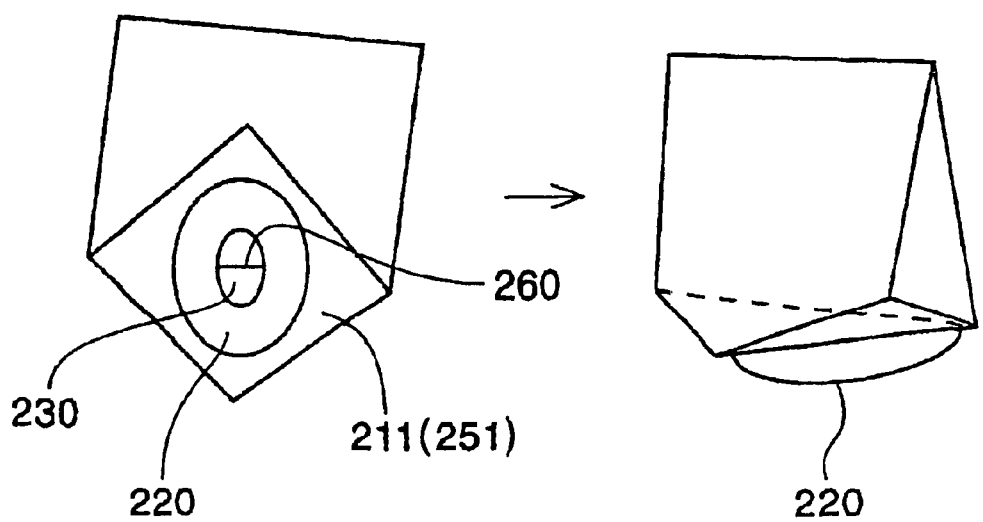
FIG. 2D is a schematic view showing processes for expanding the disposable excreta management device shown in FIGS. 2A–1C.

In the embodiment shown in FIGS. 2A–2D, the bag (210) preferably has an reversed alphabet "T"-like shape in the cross-sectional view before the bag (210) contains excreta. In addition, the bag (210) preferably has a three-dimensional shape when the bag (210) expands as shown in FIG. 2D. The bag (210) has three surfaces which are (251), (252), (253) in this embodiment. Furthermore, the bag (210) has two portions, one is a wearer facing portion (211) and the other is a garment facing portion (212). The wearer facing portion (211) is the portion of the bag (210), which comprises the opening (230) and is generally oriented towards the wearer when the excreta management device (200) is worn. The wearer facing portion (211) preferably comprises only the plane-like surface (251) before the bag (210) expands in this embodiment. Furthermore, the wearer facing portion (211) substantially forms a three-dimensional shape when the bag (210) expands completely as shown in FIG. 2D. The garment facing portion (212) is the portion of the bag (210), which is the generally oriented away from the wearer when the excreta management device (200) is worn, and towards a garment if a garment is worn. The garment facing portion (212) comprises the surfaces (252) and (253), and does not have the opening (230). In addition, the garment facing portion (212) has two corners (240, 240) opposite to the wearer facing portion (211).

The bag (210) preferably has at least one fold on the garment facing portion (212). The number of the fold will obviously depend upon the circumstances, such as a configuration of the bag, a size of the bag and a material of the bag. In the embodiment shown in FIGS. 2C and 2D, the garment facing portion (212) is folded along the fold (260). The bag (210) can expand vertically to have a three-dimensional shape when the bag (210) contains excreta, thereby ensuring better wearing comfort for a moving wearer and providing extra storage capacity in use if needed. Preferably, the fold (260) may be positioned across the opening (230) as shown in FIG. 2A when the bag (210) is folded. This enables excreta discharged toward the opening (230) to directly reach and push the fold (260) to expand the bag (210) vertically and to enter the interior of the bag (210) speedily. Alternatively, it is possible to expand the bag (210) into a three-dimensional shape easily by pulling the corner (240) after the device (200) is attached to the wearer.

The expansibility of the garment facing portion (212) is grater than that of the wearer facing portion (211). This is because the garment facing portion (212) has the fold (260) so that the bag (210) forms the three dimensional shape when the bag (210) expands, and the wearer facing portion (211) comprises only one plane-like surface (251). This structure enables the bag (210) to expand sufficiently even if the bag (210) containing excreta is pressed by wearer's body, such as buttocks and/or legs. Accordingly, it is possible to prevent leakage of excreta in the bag (210) efficiently. In this embodiment, the wearer facing portion (211) also expands so as to have three-dimensional shape when the bag (210) expands. This gives the bag (210) additional expansibility in the direction away from the wearer's body. The garment facing portion (212) may comprise elastic material, such as elastomer, rubber and polyurethane to have expansibility. The garment facing portion (212) may comprise elastic material without the fold (260), or the garment facing portion (212) comprising elastic material may have the fold (260) as well, as long as the bag (210) expands smoothly when the bag (210) contains excreta.

Figure 3A:
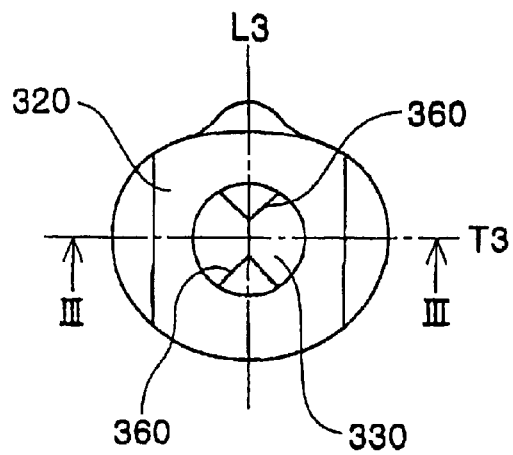
FIG. 3A is a top plan view of another embodiment of a disposable excreta management device.
Figure 3B:
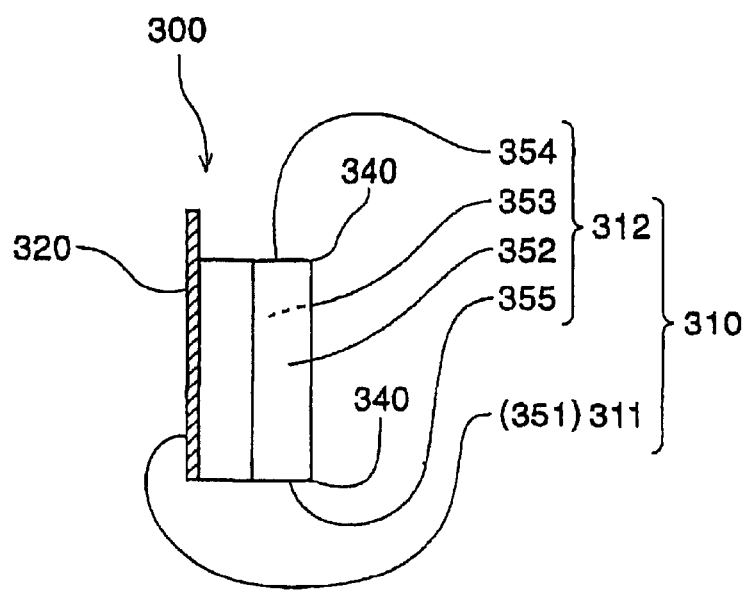
FIG. 3B is a side view of the disposable excreta management device of FIG. 3A.
Figure 3C:
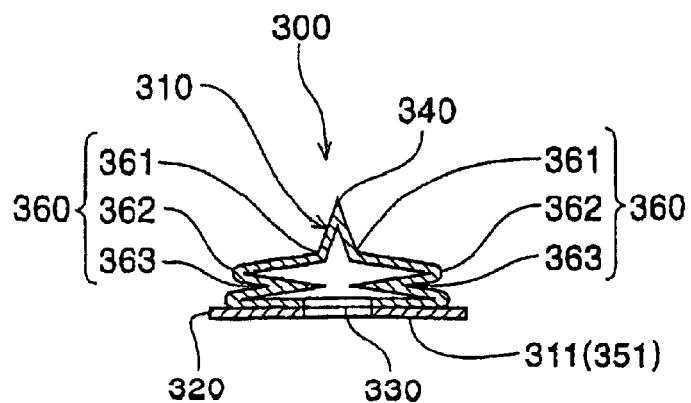
FIG. 3C is a cross-sectional view taken along line III—III of FIG. 3A.
Figure 3D:
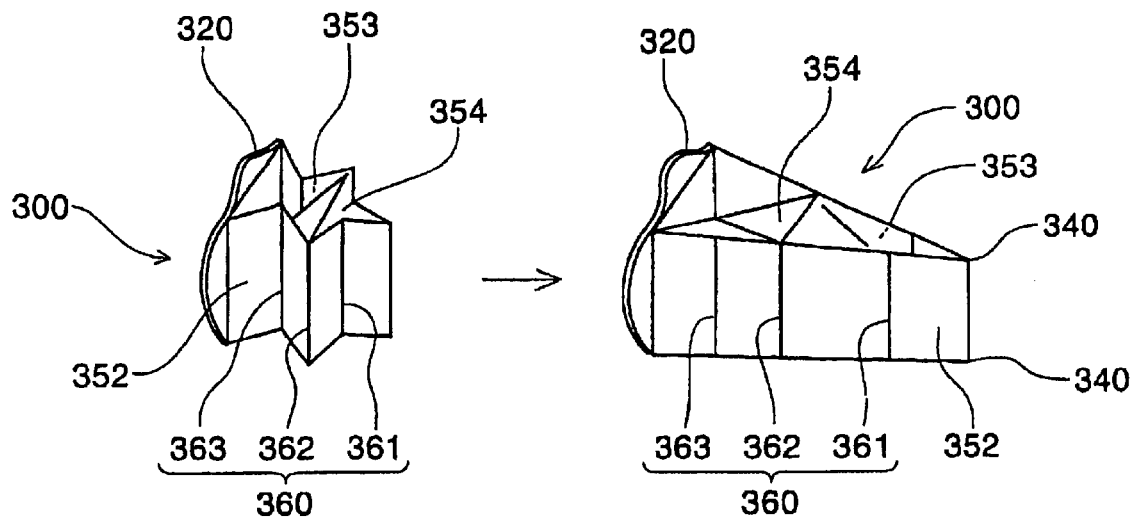
FIG. 3D is a schematic view showing processes for expanding the disposable excreta management device shown in FIGS. 3A–3C.

Referring now to FIGS. 3A–3E, there is shown another preferable embodiment of a disposable excreta management device of the present invention. As shown in FIG. 3A, the disposable excreta management device (300) has two centerlines, one is a longitudinal centerline (L3) and the other is a transverse centerline (T3). The disposable excreta management device (300) comprises a bag (310) having an opening (330) and a flange (320) surrounding the opening (330).

Figure 3E:
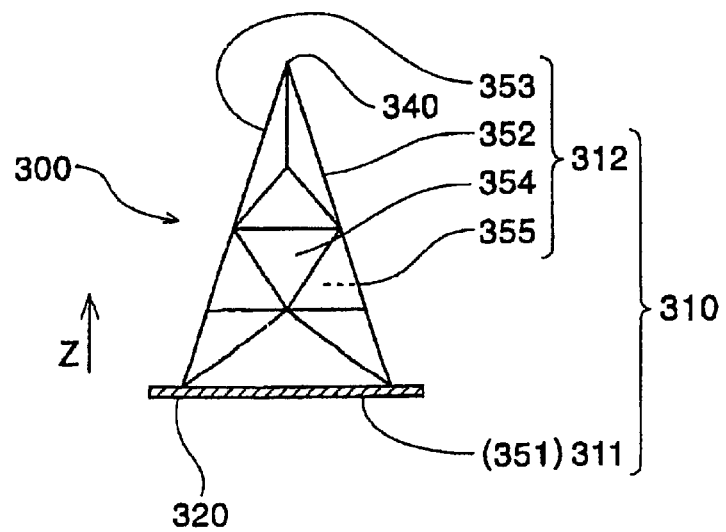
FIG. 3E is a top plan view of the disposable excreta management device shown in FIGS. 3A–3C in an expanded configuration.

In the embodiment shown in FIGS. 3–3E, the bag (310) preferably has a three-dimensional shape including two corners (340, 340). Preferably, the bag (310) has a substantial triangular prism shape as shown in FIGS. 3D and 3E, and five surfaces which are (351), (352), (353), (354) and (355) in this embodiment. Furthermore, the bag (310) has two portions, one is a wearer facing portion (311) and the other is a garment facing portion (312). The wearer facing portion (311) is the portion of the bag (310), which comprises the opening (330) and is generally oriented towards the wearer when the excreta management device (300) is worn. The wearer facing portion (311) preferably comprises only the plane-like surface (351) before the bag (310) expands in this embodiment. The garment facing portion (312) is the portion of the bag (310), which is the generally oriented away from the wearer when thie excreta management device (300) is worn, and towards a garment if a garment is worn. The garment facing portion (312) comprises the surfaces (352), (353), (354) and (355), and does not have the opening (330). In addition, the corners (340, 340) are opposite to the wearer facing portion (311).

The bag (310) preferably has at least one fold on the garment facing portion (312). The number of the fold will obviously depend upon the circumstances, such as a configuration of the bag, a size of the bag and a material of the bag. In the embodiment shown in FIGS. 3C and 3D, the garment facing portion (312) is folded along the fold (360). The bag (310) can expand vertically to have a three-dimensional shape when the bag (310) contains excreta, thereby ensuring better wearing comfort for a moving wearer and providing extra storage capacity in use if needed.

Preferably, the fold (360) may be positioned across the opening (330) as shown in FIG. 2A when the bag (310) is folded. This enables excreta discharged toward the opening (330) to directly reach and push the fold (360) to expand the bag (310) vertically and to enter the interior of the bag (310) speedily. Alternatively, it is possible to expand the bag (310) into a three-dimensional shape easily by pulling the corner (340) after the device (300) is attached to the wearer.

The expansibility of the garment facing portion (312) is grater than that of the wearer facing portion (311). This is because the garment facing portion (312) has the folds (361), (362) and (363) so that the bag (310) forms the three dimensional shape when the bag (310) expands, and the wearer facing portion (311) comprises only one plane-like surface (351). This structure enables the bag (310) to expand sufficiently even if the bag (310) containing excreta is pressed by wearer's body, such as buttocks and/or legs. Accordingly, it is possible to prevent leakage of excreta in the bag (310) efficiently. Furthermore, because the plural folds (361), (362) and (363) are formed on the garment facing portion (312), the garment facing portion (312), i.e. the bag (310), can expand sufficiently in Z direction shown in FIG. 3E. Because the expansion of the bag (310) in Z direction makes possibility, that the bag (310) is pressed by wearer's body, decrease. The garment facing portion (312) may comprise elastic material, such as elastomer, rubber and polyurethane to have expansibility. The garment facing portion (312) may comprise elastic material without the fold (360), or the garment facing portion (312) comprising elastic material may have the fold (360) as well, as long as the bag (310) expands smoothly when the bag (310) contains excreta.

Figure 4A:
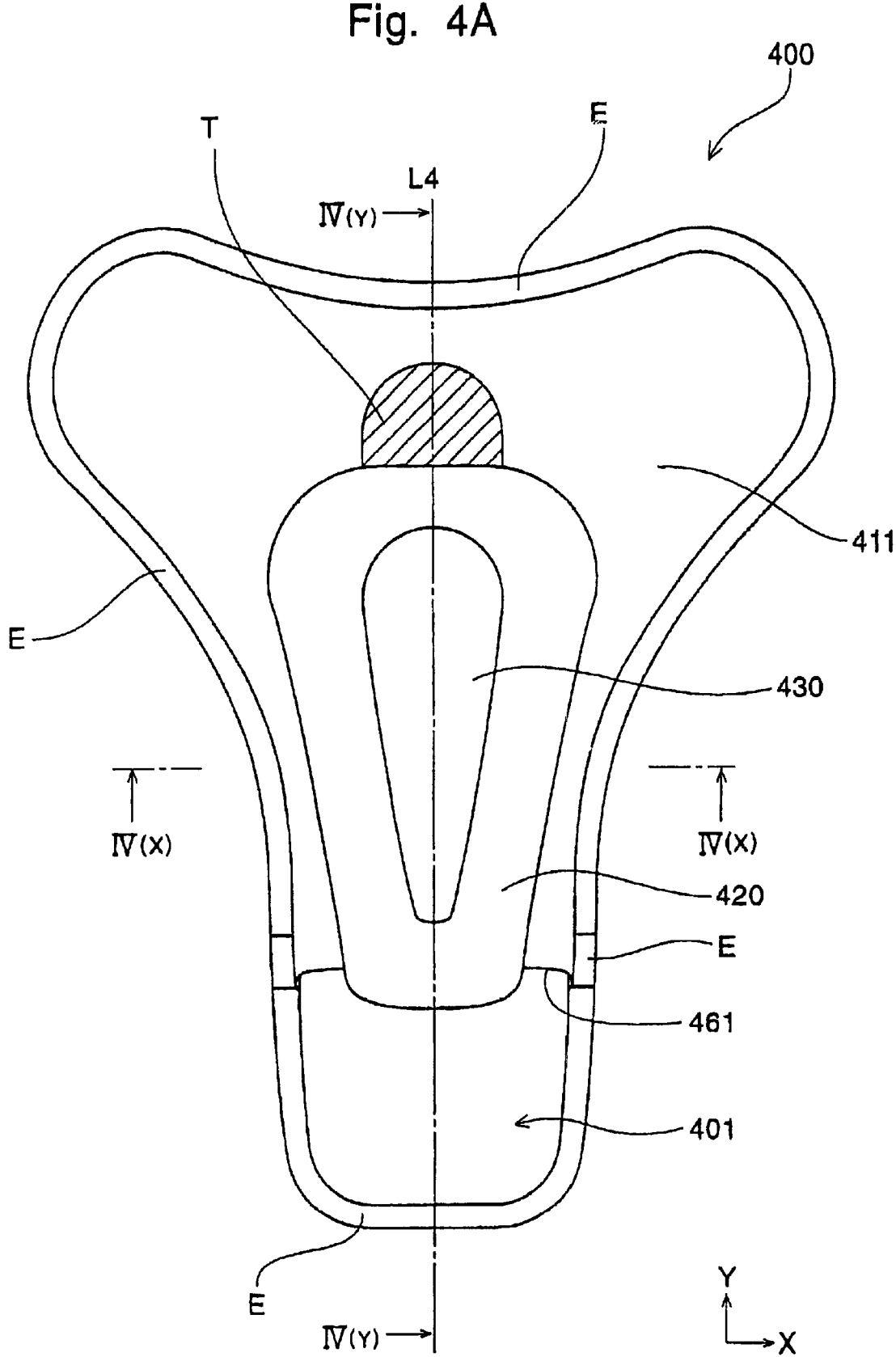
FIG. 4A is a top plan view of another embodiment of a disposable excreta management device.

Referring now to FIGS. 4A–4E, there is shown another preferable embodiment of a disposable excreta management device of the present invention. As shown in FIG. 4A, the disposable excreta management device (400) has two centerlines, one is a longitudinal centerline (L4) and the other is a transverse centerline (T4). The disposable excreta management device (400) comprises a bag (410) having an opening (430) and a flange (420) surrounding the opening (430). In addition, the bag (410) has two portions, one is a wearer facing portion (401) and the other is a garment facing portion (402). The wearer facing portion (401) is the portion of the bag (410), which comprises the opening (430) and is generally oriented towards the wearer when the excreta management device (400) is worn. The garment facing portion (402) is the portion of the bag (410), which is the generally oriented away from the wearer when the excreta management device (400) is worn, and towards a garment if a garment is worn.

In the embodiment shown in FIGS. 4A–4E, the bag (410) preferably comprises a liquid impermeable wearer facing sheet (411) positioned at the wearer facing portion (401) and a liquid impermeable garment facing sheet (412) positioned at the garment facing portion (402). Both the wearer facing sheet (411) and the garment facing sheet (412) preferably comprise a polyethylene/polypropylene film and a nonwoven which is laminated on the outside surface of the film.

The wearer facing sheet (411) and the garment facing sheet (412) are folded (tacked) so that the bag (410) can expand vertically to have a three-dimensional shape in use, thereby ensuring better wearing comfort for a moving wearer and providing extra storage capacity in use if needed. The wearer facing sheet (411) and the garment facing sheet (412) preferably have folds (461, 462) having an alphabet "Z"-like configuration in the cross-sectional view of the wearer facing sheet taken along the direction at an angle with the direction in which the fold extends as shown in FIGS. 4A–4D respectively. Such a fold is referred to as "Z-fold" herein. In the embodiment as shown in FIGS. 4A–4D, the wearer facing sheet (411) preferably has one Z-fold (461) oriented in the transverse direction (X), and furthermore, the garment facing sheet (412) preferably has one Z-fold (462) oriented in the transverse direction (X). Alternatively, the Z-fold may be oriented at an angle to the transverse direction (X). The garment facing sheet (412) also has two Z-folds (463) oriented in the longitudinal direction (Y) as shown in FIG. 4D. Preferably, the two Z-folds (463) disposed oppositely with respect to the longitudinal centerline (L4) and parallel to the longitudinal centerline (L4). Alternatively, the two Z-folds (463) may be disposed at an angle with respect to the longitudinal centerline (L4). The combination of the two opposite Z-folds has a Greek letter "Ω" like configuration in the cross-sectional view of the wearer facing sheet taken along the direction at an angle with the direction in which the folds extend as shown in FIGS. 4D and 4E. Such a combination of two opposite Z-folds is referred to as "Ω-fold (OMEGA-fold)" herein. Thus, the wearer facing sheet (411) in this embodiment comprises one Z-fold (461) as shown in FIG. 4A, and the garment facing sheet (412) comprises one Z-fold (462) and one OMEGA-fold (463) as shown in FIG. 4D. The number of Z-fold and/or OMEGA-fold on the wearer facing sheet (411) is not limited to the embodiment as shown in FIGS. 4A and/or 4D as far as the wearer facing sheet (411) and the garment facing sheet (412) can expand vertically to have a three-dimensional shape in use.

The term "Z-fold" as used hereinafter refers to folds oriented in the transverse direction (X) as shown in FIGS. 4A and 4D, and the term "OMEGA-fold" as used hereinafter refers to a pair of opposite Z-folds oriented in longitudinal direction (Y) as shown in FIG. 4D.

According to the embodiment shown in FIGS. 4A–4E, the Z-fold (462) and the OMEGA-fold (463) are formed on the garment facing portion (402). This structure enables the bag (410) to expand sufficiently even if the bag (410) containing excreta is pressed by wearer's body, such as buttocks and/or legs. Accordingly, it is possible to prevent leakage of excreta in the bag (410) efficiently. Preferably, the number of Z-fold and/or OMEGA-fold on the garment facing portion (402) is greater than the number of Z-fold and/or OMEGA-fold on the wearer facing portion (401), or the Z-fold and/or the OMEGA-fold may not be formed on the wearer facing portion (401) as far as at least one Z-fold or OMEGA-fold is formed on the garment facing portion (402). These structures mean that the expansibility of the garment facing portion (402) is grater than that of the wearer facing portion (401). Therefore, these structures enable the bag (410) to expand speedily even if the bag (410) containing excreta is pressed by wearer's body, such as buttocks and/or legs. This is because the garment facing portion (402) expands more speedily/sufficiently than the wearer facing portion (401) when the bag (410) contains excreta. The number of the folds (461), (463), (462) and/or (464) will obviously depend upon the circumstances, such as a configuration of the bag, a size of the bag and a material of the bag, as log as the garment facing portion (402) can expand speedily when the bag (410) contains excreta.

As shown in FIG. 4A, the wearer facing sheet (411) is provided with an opening (430) whereby excreta such as urine and/or bowel movement is received from the body prior to storage within the bag cavity. The opening (430) is surrounded by a flange (420) and may be provided in any shape or size, such as circular, oblong, heart shaped and may be symmetrical or asymmetrical, preferably the opening has an oblong configuration either in the longitudinal or in the transversal direction.

Figure 4B:
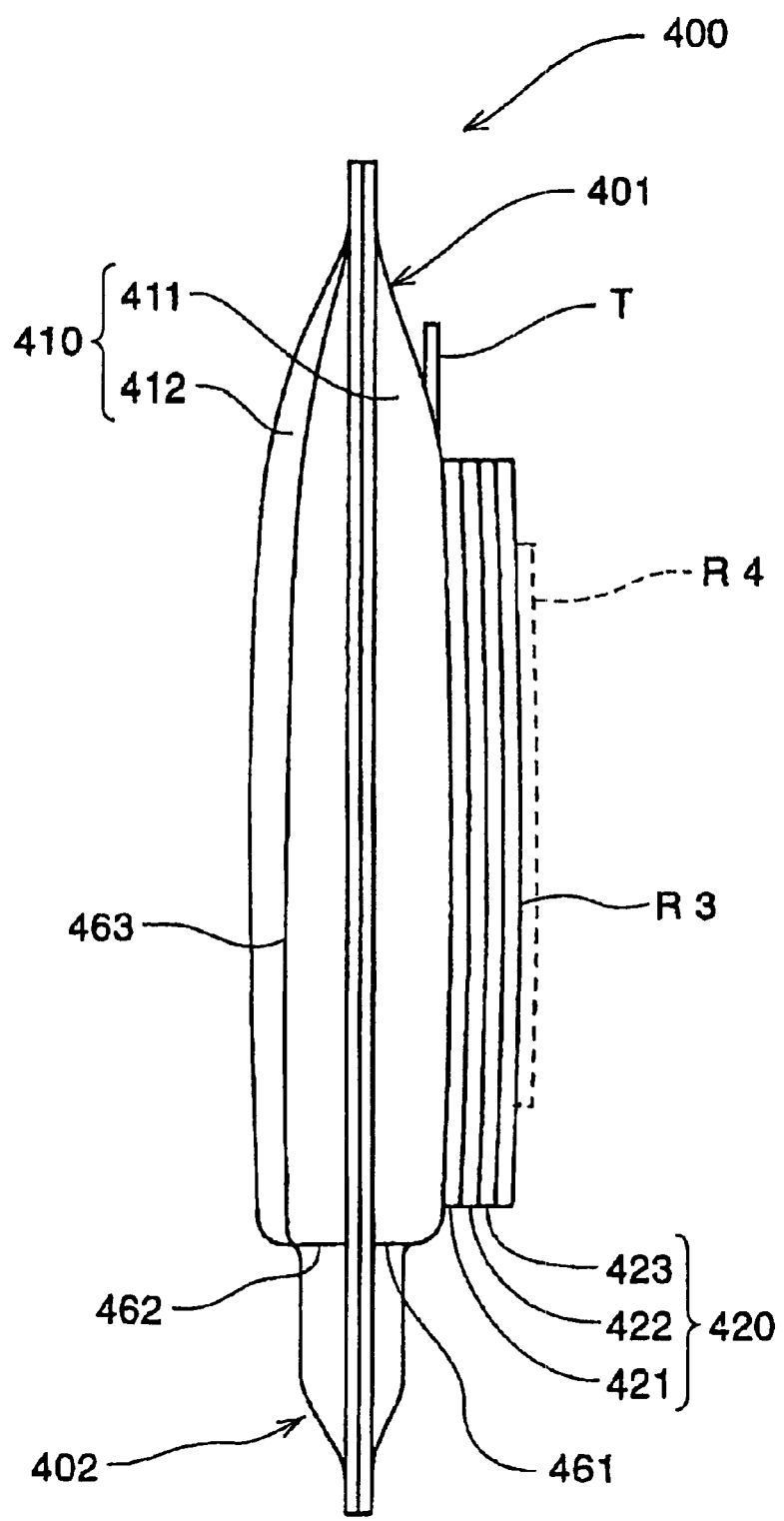
FIG. 4B is a side view of the disposable excreta management device of FIG. 4A.
Figure 4C:
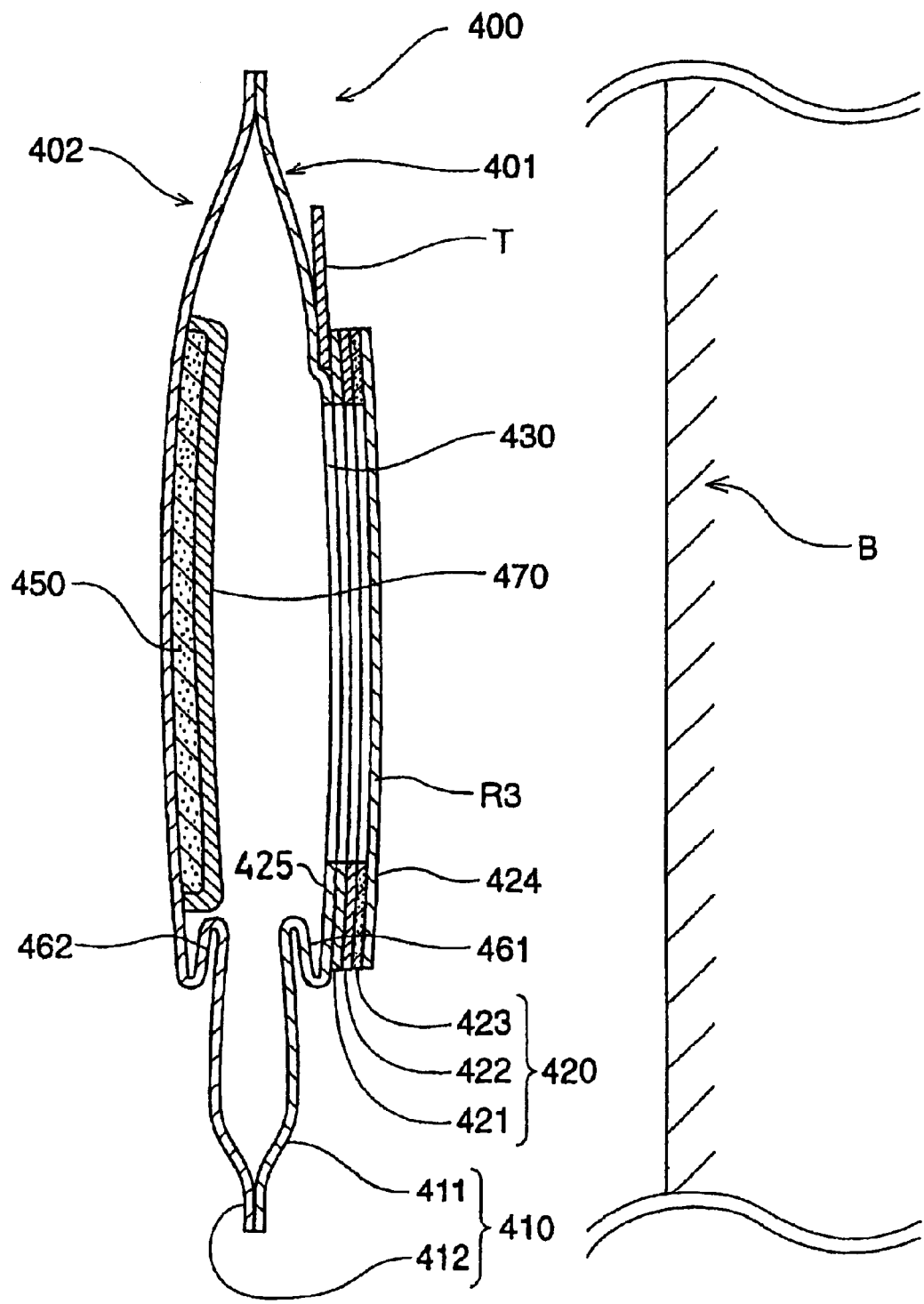
FIG. 4C is a cross-sectional view taken along line IV(y)—IV(y) of FIG. 4A.
Figure 4D:
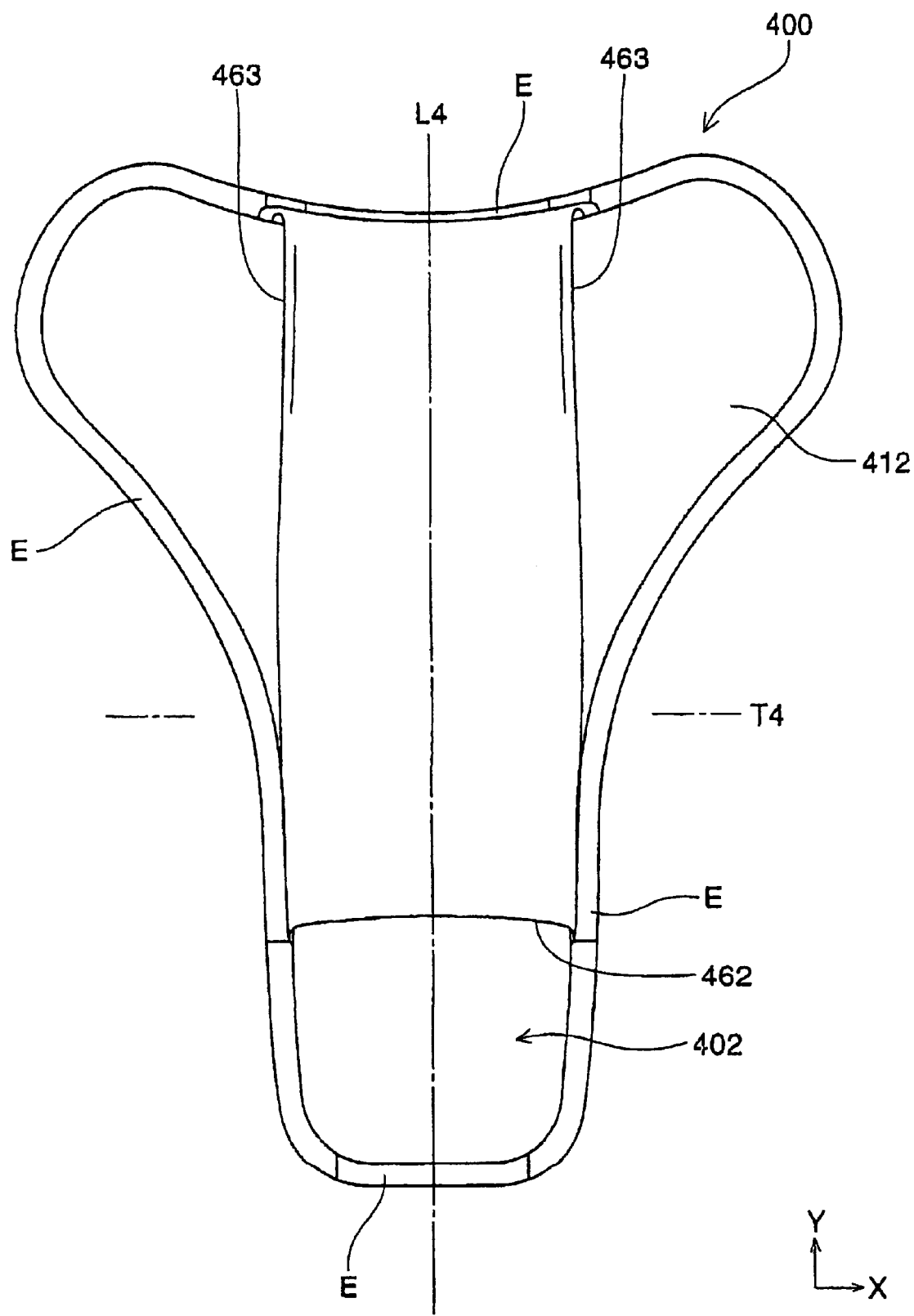
FIG. 4D is a FIG. 4A is a bottom plan view of the disposable excreta management device of FIG. 4A.
Figure 4E:
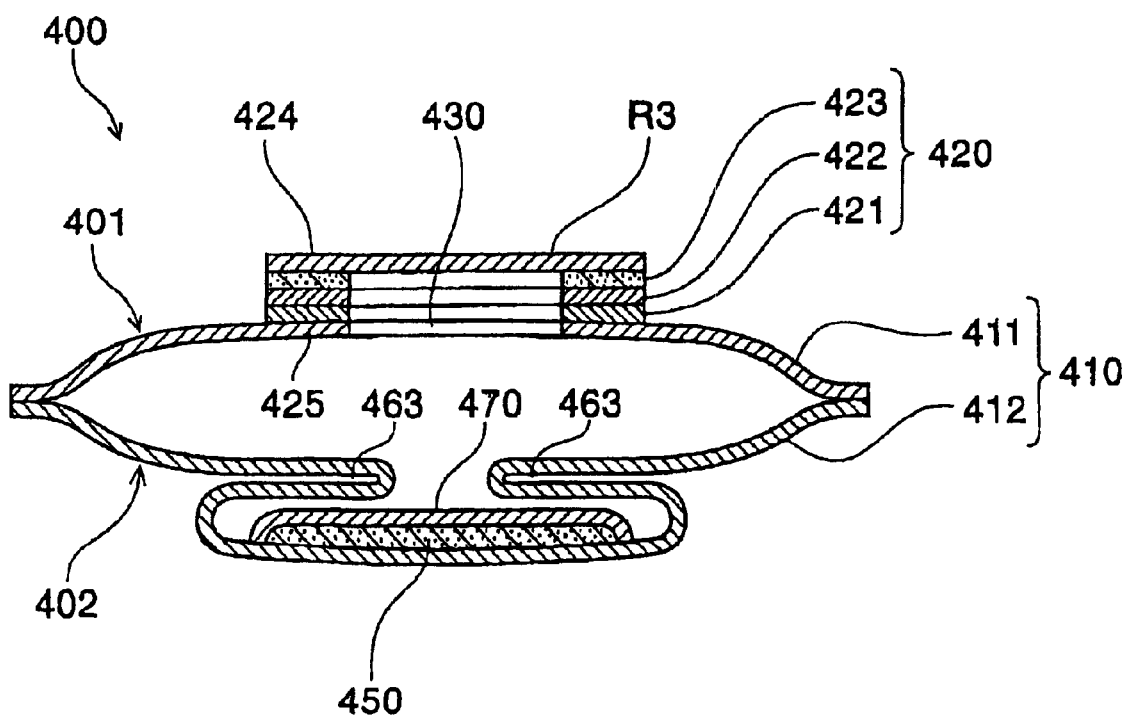
FIG. 4E is a cross-sectional view taken along line IV(x)—IV(x) of FIG. 4A.

As shown in FIGS. 4A–4C and 4E, the flange (420) (or adhesive flange) is provided at the periphery of the opening (430) to attach the device (400) to the wearer's body (B). The adhesive flange (420) has a wearer facing side (424) and an opposed garment facing side (425) as shown in FIGS. 4C and 4E. In a preferred embodiment, these are two large, substantially flat surfaces of the adhesive flange (420). The adhesive flange (420) may be provided in any size depending on the wearer group for which the device is intended. The adhesive flange (420) may be provided in any shape and preferably has a symmetrical, slightly oblong shape.

In the embodiment as shown in FIGS. 4A–4E, the adhesive flange (420) may comprise a nonwoven layer (421), a polyurethane layer (422) and an adhesive layer (423) in its order from the wearer facing sheet (411) towards the wearer's body (B) as shown in FIG. 4C. In this embodiment, both the nonwoven layer (421) and the polyurethane layer (422) may be provided as a substrate in order to support the adhesive layer (423), or a substrate may comprise either of them. Particularly, the polyurethane layer (422) may be provided in order to adapt the devise (400) to the movement of the wearer during use of the device (400).

The wearer facing side (424) of the adhesive flange (420) comprises a body-compatible adhesive such as the adhesive layer (423) as shown in FIGS. 4B, 4C and 4E. The adhesive layer (423) is used in order to fix the device (400) with the wearer's body (B). In the embodiment as shown in FIGS. 4A–4E, the adhesive layer (423) is preferably covered with a release film (R3) to protect the adhesive layer (42C) from contamination before use, such as siliconized paper or film. If the opening (430) is formed thorough the release film (R3) for the manufacturing reason, a second release film (R4) designated by the broken line in FIG. 4B may be added so that foreign objects do not enter into the bag (410) before use of the device (400). The adhesive layer (423) may cover the entire wearer facing surface of the flange, or alternatively have at least one, preferably two to six non-adhesive portions. These portions may be adhesive free or may contain inactivated or covered adhesives.

Preferably, a tab (T) is applied on the adhesive flange (420) in order to remove the device (400) from the wearer's body (B) easily. The tab (T) helps users remove the device (400) from the wearer's body.

The adhesive flange (420) is attached to the wearer facing sheet (411) by means known to the man skilled in the art, such as adhesives.

An absorbent material (450) is contained within the bag (410). I.e., the absorbent material (450) is positioned between the wearer facing sheet (411) and the garment facing sheet (412) as shown in FIGS. 4C and 4E. The absorbent material (450) may be positioned in the bag (410) in any suitable manner. For example, the absorbent material (450) may be loosely arranged within the bag (410) or may be secured to the inner side of the garment facing sheet (412). Any known techniques for securing absorbent material to nonwoven and film substrates may be used to secure the absorbent material (450) to the inner layer of the bag (410). The absorbent material (450) may also be arranged to have any desired shape or configuration (e.g., rectangular, oval, circular, etc.). The absorbent material (450) may comprise any absorbent material which is capable of absorbing and retaining liquids such as urine. The absorbent material (450) may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers, synthetic fibers such as crimped polyester fibers; peat moss; tissue, including tissue wraps and tissue laminates; absorbent foams; absorbent sponges; superabsorbent polymers; superabsorbent hydrogel-forming polymeric material; absorbent gelling materials; or any other known absorbent material or combinations of materials or mixtures of these. The configuration and construction of the absorbent component may also be varied (e.g., the absorbent component may have varying caliper zones (e.g., profiled so as to be thicker in the center), hydrophilic gradients, superabsorbent gradients, or may comprise one or more layers or structures.

In the embodiment, the device (400) also has a liquid-permeable topsheet (470) to cover the absorbent material (450) as shown in FIGS. 4C and 4E. The liquid impermeable wearer facing sheet (411), the liquid-permeable topsheet (470) and the liquid-impermeable garment facing sheet (412) are preferably joined at the periphery edge (E) of the device (400) by any means known in the art, such as a heat seal.

The liquid-permeable topsheet (470) is preferably compliant, soft feeling, and non-irritating to the wearer's skin. A suitable liquid-permeable topsheet (470) may be, manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. The liquid-permeable topsheet (470) is preferably made of a hydrophobic material to isolate the wearer's skin from body fluids (e.g. urine) which have absorbed in the absorbent material (450). However, in case body fluid discharged from the wearer is accidentally deposited on the liquid-permeable topsheet (470), at least the upper surface of the liquid-permeable topsheet (470) may be treated to be hydrophilic so that liquids will transfer through liquid-permeable topsheet (470) more rapidly. This diminishes the likelihood that body fluid will flow off the liquid-permeable topsheet (470) rather than being drawn through the liquid-permeable topsheet (470) and being absorbed by the absorbent material (450). The liquid-permeable topsheet (470) can be rendered hydrophilic by treating it with a surfactant. Suitable methods for treating the liquid-permeable topsheet (470) with a surfactant include spraying the liquid-permeable topsheet (470) material with the surfactant and immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al on Jan. 29, 1991 and U.S. Pat. No. 4,988,345 entitled "Absorbent Articles with Rapid Acquiring Absorbent Cores" issued to Reising on Jan. 29, 1991. Alternatively, surfactant may be impregnated into the fibers or resin and the topsheet 28 may be formed by the fibers with impregnated surfactant.

Although the embodiment shown in FIGS. 4A–4E is about a disposable excreta management device containing the absorbent material into its bag, the present invention can be also applied to another excreta management devices (500) not containing the absorbent material into the bag (510) as shown in FIGS. 5A–5C. Referring now to FIGS. 5A–5C, there is shown another preferable embodiment of a disposable excreta management device of the present invention.

In the embodiment, the device (500) has a longitudinal centerline (L5) and a transverse centerline (T5) as shown in FIG. 5A. The disposable excreta management device (500) comprises a bag (510) having an opening (530) and a flange (520) surrounding the opening (530). In addition, the bag (510) has two portions, one is a wearer facing portion (501) and the other is a garment facing portion (502). The wearer facing portion (501) is the portion of the bag (510), which comprises the opening (530) and is generally oriented towards the wearer when the excreta management device (500) is worn. The garment facing portion (502) is the portion of the bag (510), which is the generally oriented away from the wearer when the excreta management device (500) is worn, and towards a garment if a garment is worn.

In the embodiment shown in FIGS. 5A–5C, the bag (510) preferably comprises a liquid impermeable wearer facing sheet (511) positioned at the wearer facing portion (501) and a liquid impermeable garment facing sheet (512) positioned at the garment facing portion (502). Both the wearer facing sheet (511) and the garment facing sheet (512) preferably comprise a polyethylene/polypropylene film and a nonwoven which is laminated on the outside surface of the film. The liquid impermeable wearer facing sheet (511) and the liquid-impermeable garment facing sheet (512) are preferably joined at the periphery edge (E) of the device (500) by any means known in the art, such as a heat seal. The Z-fold (561) is formed on the wearer facing sheet (511). In addition, the OMEGA-fold (562) is formed on the garment facing sheet (512). Preferably, expansibility of the garment facing portion (502) having the OMEGA-fold (562) is greater than that of the wearer facing portion (501) having the Z-fold (561). This structure enables the bag (510) to expand speedily even if the bag (510) containing excreta is pressed by wearer's body, such as buttocks and/or legs. The device (500) does not have an absorbent material unlike the above-mentioned disposable excreta management device (400) as shown in FIGS. 4A–4E. The device (500) can have a big capacity of the bag to contain excreta because the absorbent material is not provided into the bag (510). This structure is useful for entrapping and immediately containing high viscosity excreta, such as bowel movement.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable excreta management device having a longitudinal centerline and a transverse centerline, the disposable excreta management device comprising a flexible bag to contain excreta and an adhesive flange to attach the device to the body of the wearer, the flexible bag having a wearer facing portion and a garment facing portion, the wearer facing portion having an opening surrounded by the adhesive flange, wherein the garment facing portion of the flexible bag has an expansibility which is greater than that of the wearer facing portion of the flexible bag when the flexible bag contains excreta.

2. A disposable excreta management device according to claim 1 wherein the garment facing portion of the flexible bag comprises one or more folds.

3. A disposable excreta management device according to claim 2 wherein one of the folds is positioned across the opening before the flexible bag contains excreta.

4. A disposable excreta management device according to claim 1 wherein the device comprises an absorbent material placed between the wearer facing portion and the garment facing portion, and a liquid permeable sheet placed between the wearer facing portion and the absorbent material.

5. A disposable excreta management device having a longitudinal centerline and a transverse centerline, the disposable excreta management device comprising a flexible bag to contain excreta and an adhesive flange to attach the device to the body of the wearer, wherein the flexible bag comprises a plane-like wearer facing portion and a garment facing portion having a three-dimensional shape, and the wearer facing portion has an opening surrounded by the adhesive flange.

6. A disposable excreta management device according to claim 5 wherein the garment facing portion is folded on the plane-like wearer facing portion before the flexible bag contains excreta.

7. A disposable excreta management device according to claim 5 wherein the fold of the garment facing portion is positioned across the opening before the flexible bag contains excreta.

8. A disposable excreta management device according to claim 5 wherein the garment facing portion has one or more corners opposite to the plane-like wearer facing portion.

9. A disposable excreta management device according to claim 5 wherein the flexible bag has a substantial polyhedron shape.

* * * * *